United States Patent [19]

Bamberg et al.

[11] 4,089,963
[45] May 16, 1978

[54] ESTERS OF AMIDINOPENICILLANIC ACIDS, PHARMACEUTICAL PREPARATIONS AND METHOD FOR TREATING INFECTIOUS DISEASES

[75] Inventors: Peter Bamberg, Enhorna; Bertil Ake Ekstrom; Berndt Olof Harald Sjoberg, both of Sodertalje, all of Sweden

[73] Assignee: Astra Pharmaceutical Products, Inc., Framingham, Mass.

[21] Appl. No.: 585,757

[22] Filed: Jun. 10, 1975

Related U.S. Application Data

[63] Continuation-in-part of Ser. No. 340,674, Mar. 13, 1973, abandoned.

[51] Int. Cl.$^2$ .................... A61K 31/43; C07D 499/02; C07D 499/32
[52] U.S. Cl. ................................. 424/270; 260/239.1; 260/306.7 C; 424/271; 542/420
[58] Field of Search .................... 260/239.1, 306.7 C, 260/240 G; 424/270, 271

[56] References Cited

U.S. PATENT DOCUMENTS

| | | | |
|---|---|---|---|
| 3,697,507 | 10/1972 | Frederiksen et al. | 260/239.1 |
| 3,873,521 | 3/1975 | Ekström et al. | 260/239.1 |
| 3,957,764 | 5/1976 | Lund | 260/240 G |

FOREIGN PATENT DOCUMENTS

| | | | |
|---|---|---|---|
| 784,800 | 10/1972 | Belgium | 260/239.1 |
| 1,293,590 | 10/1972 | United Kingdom | 260/239.1 |

*Primary Examiner*—Gerald A. Schwartz
*Attorney, Agent, or Firm*—Brumbaugh, Graves, Donohue & Raymond

[57] ABSTRACT

New esters of amidinopenicillanic acids of the formula

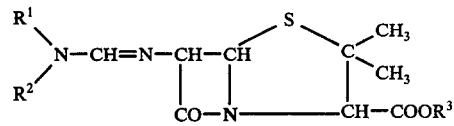

wherein each of $R^1$ and $R^2$, which are the same or different, is a saturated or unsaturated alkyl group, a cycloalkyl, or cycloalkyl-alkyl group, or wherein $R^1$ and $R^2$, together with the adjacent nitrogen atom, form a heterocyclic ring system; $R^3$ is the radical

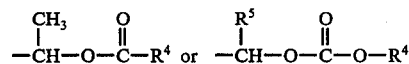

in which radicals $R^4$ is an alkyl, phenyl, or substituted phenyl; and $R^5$ is hydrogen or methyl, useful as active ingredients in pharmaceutical preparation and methods for the treatment of infectious diseases.

22 Claims, No Drawings

ESTERS OF AMIDINOPENICILLANIC ACIDS, PHARMACEUTICAL PREPARATIONS AND METHOD FOR TREATING INFECTIOUS DISEASES

This application is a continuation-in-part of the applicants' previous copending application Ser. No. 340,674 filed Mar. 13, 1973, now abandoned.

The present invention relates to new penicillanic acid derivatives which are effective in the treatment of infectious diseases caused by bacterial microorganisms. The invention also relates to the preparation of pharmaceutical preparations containing these new penicillins and to methods for their pharmacological use.

More precisely, this invention relates to new esters of amidinopenicillanic acids of the formula

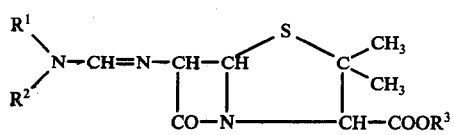   I and therapeutically acceptable salts thereof, wherein $R^1$ and $R^2$, which are the same or different, are selected from the group consisting of saturated or unsaturated alkyl groups containing from 1 to 10 carbon atoms, cycloalkyl groups containing from 3 to 7 carbon atoms, and cycloalkyl-alkyl groups containing from 4 to 10 carbon atoms, or wherein $R^1$ and $R^2$, together with the adjacent nitrogen atom, form a heterocyclic ring system; $R^3$ is

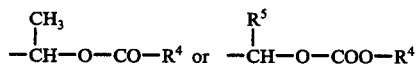

in which radicals $R^4$ is selected from the group consisting of alkyl groups containing from 1 to 8 carbon atoms, substituted with amino groups, halogen, or alkoxy groups containing from 1 to 4 carbon atoms; and $R^5$ is hydrogen or methyl.

Illustrative examples of radicals included in the above definitions are:

alkyl: methyl, ethyl, propyl, isopropyl, butyl, isobutyl, pentyl, hexyl, heptyl, octyl, 2-ethyl-hexyl;

cycloalkyl: cyclopropyl, cyclobutyl, cyclopentyl, cyclohexyl, cycloheptyl;

cycloalkyl-alkyl:

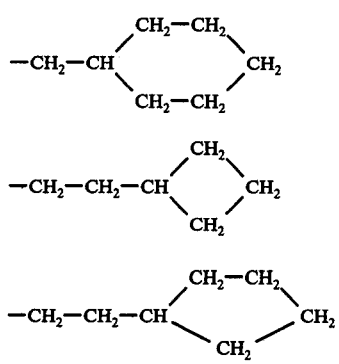

alkoxy: methoxy, ethoxy, propyloxy, isopropyloxy, butoxy, isobutoxy;

Halogen: F, Cl, Br;

$-NR^1R^2$ forming a heterocyclic ring system:

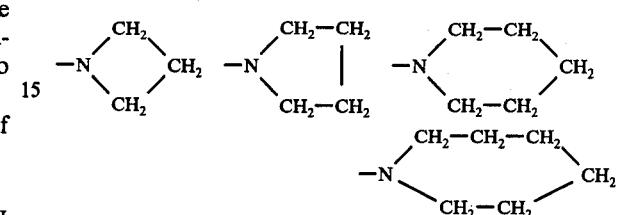

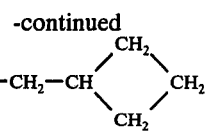

The above examples illustrate, where applicable, all the radicals $R^1$-$R^4$ to the extent of the definition given to each radical and within the boundaries with regard to number of carbon atoms which may be prescribed for each radical.

Preferred compounds, according to the invention, are as follows:

(a) compounds of formula I, and therapeutically acceptable salts thereof, wherein $R^1$ and $R^2$ are the same or different and selected from the group consisting of saturated or unsaturated alkyl groups containing from 1 to 10 carbon atoms, cycloalkyl groups containing from 3 to 7 carbon atoms; and cycloalkyl-alkyl groups containing from 4 to 10 carbon atoms; $R^4$ is an alkyl group containing from 1 to 8 carbon atoms; and $R^5$ is hydrogen or methyl;

(b) compounds of formula I, and therapeutically acceptable salts thereof, wherein $R^1$ and $R^2$, together with the adjacent nitrogen atom, form a heterocyclic ring structure; $R^4$ is phenyl or phenyl substituted with amino groups, halogen, or alkoxy groups containing from 1 to 4 carbon atoms; and $R^5$ is hydrogen or methyl;

(c) compounds of formula I, and therapeutically acceptable salts thereof, wherein $R^1$ and $R^2$ are the same or different and selected from the group consisting of saturated or unsaturated alkyl groups containing from 1 to 10 carbon atoms, cycloalkyl groups containing from 3 to 7 carbon atoms, and cycloalkyl-alkyl groups containing from 4 to 10 carbon atoms; $R^4$ is phenyl or phenyl substituted with amino groups, halogen, or alkoxy groups containing from 1 to 4 carbon atoms; and $R^5$ is hydrogen or methyl;

(d) compounds of formula I, and therapeutically acceptable salts thereof, wherein $R^1$ and $R^2$, together with the adjacent nitrogen atom, form a heterocyclic ring structure; $R^4$ is an alkyl group containing from 1 to 8 carbon atoms; and $R^5$ is hydrogen or methyl.

The compounds of the invention are of value in the treatment of infectious diseases in man or animals caused by bacterial organisms. They may be isolated and used as such, but also, depending on the presence of basic or acidic groups in the molecule, in the form of salts with pharmaceutically acceptable organic or inorganic acids or bases. Examples of suitable acids are hydrochloric acid, hydrobromic acid, sulphuric acid, phosphoric acid, acetic acid, tartaric acid, citric acid, and fumaric acid. Examples of suitable bases are sodium hydroxide, potassium hydroxide, calcium hydroxide, aluminum hydroxide, ammonium hydroxide, non-toxic amines, such as trialkylamines, including triethylamine, procaine, dibenzylamine, N-benzyl-β-phenethylamine, 1-ephenamine, N,N¹-dibenzylethylene-diamine, dehydroabiethylamine, N,N¹-bis-dehydroabiethylethylenediamine, N-(lower)-alkylpiperidine (e.g., N-ethylpiperidine), and other bases which have been used for the preparation of salts with penicillins.

The side chain of the structure in formula I may contain an asymmetric center. Depending on the configuration around this center, the compound will occur in different diastereoisomeric forms which are all biologically active. Likewise, the ester groups may contain asymmetric atoms, e.g., when $R^5$ = $CH_3$ or $C_2H_5$, giving rise to different diastereoisomeric forms, which also are all biologically active. It is to be understood that the invention comprises the pure diastereoisomers, as well as mixtures of them.

Penicillanic acid derivatives of general formula II

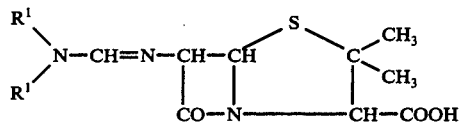

are known to have strong anti-bacterial activity, especially against gram-negative organisms (Netherlands patent No. 70 16435). They are, however, not well-absorbed by the oral route and have to be given by injection. It is one purpose of the present invention to provide esters of compounds of formula II, which are well-absorbed orally and hydrolyzed within the body to give blood and organ levels of the compounds of formula II that are adequate for the treatment of infectious diseases caused by bacteria sensitive to penicillanic acids of general formula II. To achieve the full anti-bacterial activity of the penicillanic acids II, it is necessary to choose such ester groups that are rapidly hydrolyzed in vivo. It is an essential feature of the present invention to provide such ester groups that are rapidly hydrolyzed in the body after oral absorption.

The compounds of the invention with formula I are well-tolerated, give a low frequency of side effects, and may readily be used in pharmaceutical preparations, either as such or in the form of their salts, and they can be intermixed with solid carriers or adjuvants or both. In such preparations, the ratio between the therapeutic substance and the carriers and adjuvants may vary between about 1% and about 99%. The preparation may either be processed to, for instance, tablets, pills, or dragees, or can be supplied to medical containers, such as capsules or, as regards mixtures, they can be filled in bottles. Pharmaceutically acceptable, organic or inorganic, solid or liquid carriers may be used, suitably for oral or enteral administration or for topical application, in manufacturing the preparations. Gelatine, lactose, starch, magnesium stearate, talc, vegetabilic and animalic fats and oils, vegetabilic rubber, and polyalkylene glycol, and other known carriers for pharmaceuticals, are all suitable for manufacturing preparations of said compounds. Moreover, the preparation may contain other pharmaceutically active components, being suitably administratable together with the compounds of the invention when treating infectious diseases. For instance, other suitable antibiotical substances are gentamycin and polymyxin.

In the treatment of bacterial infections in man, the compounds of the invention are, for example, administered in amounts corresponding to 5 to 20 mg/kg/day, preferably in the range of 10 to 100 mg/kg/day, in divided dosages, e.g., two, three, or four times a day. They are administered in dosage units containing, e.g., 175, 350, 500, and 1,000 mg of the compounds.

Examples of preferred compounds of the invention are given in Tables 1–4. The designations Me and Et in the tables mean methyl and ethyl, respectively.

TABLE I

| $R^1$ | $R^2$ | $R^3$ |
|---|---|---|
| ethyl | ethyl | CH(Me)OCOMe |
| propyl | propyl | " |
| ethyl | isopropyl | " |
| isopropyl | isopropyl | " |
| allyl | allyl | " |
| methyl | n. butyl | " |
| ethyl | t. butyl | " |
| methyl | cyclopentyl | " |
| methyl | cyclohexyl | " |
| ethyl | cyclohexyl | " |
| methyl | cycloheptyl | " |
| methyl | cyclohexylmethyl | " |
| n. heptyl | n. heptyl | " |
| methyl | methyl | " |
| $R^1R^2N$— | | $R^3$ |
| pyrrolidyl-1 | | CH(Me)OCOMe |
| 2-methylpiperidyl-1 | | " |
| 3-methylpiperidyl-1 | | " |
| 4-methylpiperidyl-1 | | " |
| 2,6-dimethylpiperidyl-1 | | " |
| hexahydro-1H-azepin-1-yl | | " |
| hexahydro-1H-azepin-1-yl | | " |
| hexahydro-1(2H)-azocinyl | | " |
| 1,2,3,4-tetrahydroisoquinolyl-2 | | " |
| 4-methylpiperazinyl-1- | | " |
| morfolinyl-4 | | " |

TABLE 2

| $R^1$ | $R^2$ | $R^3$ |
|---|---|---|
| ethyl | ethyl | $CH_2OCOOEt$ |
| propyl | propyl | " |
| ethyl | isopropyl | " |
| isopropyl | isopropyl | " |
| allyl | allyl | " |
| methyl | n. butyl | " |
| ethyl | t. butyl | " |
| methyl | cyclopentyl | " |
| methyl | cyclohexyl | " |
| ethyl | cyclohexyl | " |
| methyl | cycloheptyl | " |
| methyl | cyclohexylmethyl | " |
| n. heptyl | n. heptyl | " |
| methyl | methyl | " |
| $R^1R^2N$— | | $R^3$ |
| pyrrolidyl-1 | | $CH_2OCOOEt$ |
| 2-methylpiperidyl-1 | | " |
| 3-methylpiperidyl-1 | | " |
| 4-methylpiperidyl-1 | | " |
| 2,6-dimethylpiperidyl-1 | | " |
| hexahydro-1H-azepin-1-yl | | " |
| hexahydro-1H-azepin-1-yl | | " |
| hexahydro-1(2H)-azocinyl | | " |
| 1,2,3,4-tetrahydroisoquinolyl-2 | | " |
| 4-methylpiperazinyl-1 | | " |
| morfolinyl-4 | | " |

TABLE 3

| $R^1$ | $R^2$ | $R^3$ |
|---|---|---|
| ethyl | ethyl | CH(Me)OCOOEt |
| propyl | propyl | " |
| ethyl | isopropyl | " |
| isopropyl | isopropyl | " |
| allyl | allyl | " |
| methyl | n. butyl | " |
| ethyl | t. butyl | " |
| methyl | cyclopentyl | " |

TABLE 3-continued

| $R^1$ | $R^2$ | |
|---|---|---|
| methyl | cyclohexyl | " |
| ethyl | cyclohexyl | " |
| methyl | cycloheptyl | " |
| methyl | cyclohexylmethyl | " |
| n. heptyl | n. heptyl | " |
| methyl | methyl | " |

| $R^1R^2N-$ | $R^3$ |
|---|---|
| pyrrolidyl-1 | CH(Me)OCOOEt |
| 2-methylpiperidyl-1 | " |
| 3-methylpiperidyl-1 | " |
| 4-methylpiperidyl-1 | " |
| 2,6-dimethylpiperidyl-1 | " |
| hexahydro-1H-azepin-1-yl | " |
| hexahydro-1H-azepin-1-yl | " |
| hexahydro-1(2H)-azocinyl | " |
| 1,2,3,4-tetrahydroisoquinolyl-2- | " |
| 4-methylpiperazinyl-1 | " |
| morfolinyl-4 | " |

TABLE 4

| $R^1$ | $R^2$ | $R^3$ |
|---|---|---|
| ethyl | ethyl | CH$_2$OCOOpropyl |
| propyl | propyl | " |
| ethyl | isopropyl | " |
| isopropyl | isopropyl | CH(Me)OCOOpropyl |
| allyl | allyl | " |
| methyl | n. butyl | " |
| ethyl | t. butyl | " |
| methyl | cyclopentyl | " |
| methyl | cyclohexyl | " |
| ethyl | cyclohexyl | CH(Me)OCOOi-butyl |
| methyl | cycloheptyl | " |
| methyl | cyclohexylmethyl | " |
| n. heptyl | n. heptyl | CH(Me)OCOOn-hexyl |
| methyl | methyl | CH(Me)OCOOCH$_2$CH$_2$NH$_2$ |

| $R^1R^2N-$ | $R^3$ |
|---|---|
| pyrrolidyl-1 | CH(Me)OCOCH$_2$CH$_2$NHMe |
| 2-methylpiperidyl-1 | " |
| 3-methylpiperidyl-1 | " |
| 4-methylpiperidyl-1 | CH$_2$OCOOCH$_2$CH$_2$NEt$_2$ |
| 2,6-dimethylpiperidyl-1 | " |
| hexahydro-1H-azepin-1-yl | |
| hexahydro-1H-azepin-1-yl | CH$_2$OCOOCH$_2$CH$_2$NH$_2$ |
| hexahydro-1(2H)-azocinyl | " |
| 1,2,3,4-tetrahydroisoquinolyl-2 | CH$_2$OCOOCH$_2$CH$_2$NHMe |
| 4-methylpiperazinyl-1 | " |
| morfolinyl-4 | " |

The compounds of the invention are prepared by different methods, such as by reacting a reactive derivative of an amide or thioamide of formula III

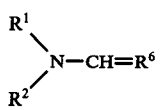   III where $R^1$ and $R^2$ are as defined above, and R is O or S, with an ester of 6-aminopenicillanic acid with formula IV

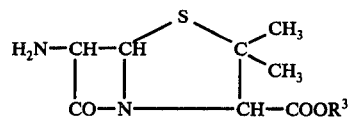   IV where $R^3$ is as defined above.

The reactive derivatives of the amides or thioamides with formula III are acid amide halogenides or dialkylsulphate complexes of acid amide acetals and may be obtained, according to known methods, by treatment of compounds of formula III with halogenating agents, such as phosgen, oxalyldichloride, thionyl chloride, or thionyl bromide, or with a dialkylsulphate, such as dimethyl sulphate. The reactions with the halogenating agents are performed in inert dry organic solvents, such as diethylether, toluene, benzene, chloroform, or carbon tetrachloride. The halogenides are usually obtained as hygroscopic precipitates.

Treatment of the acid amide dialkylsulphate complexes with strong bases, e.g., sodium methoxide, convert them into acid amide acetals of formula V

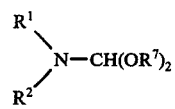   V where $R^7$ is a lower alkyl group originating from the dialkylsulphate, which also can be reacted with the esters of 6-aminopenicillanic acid with formula IV to give the compounds of the invention.

The esters of 6-aminopenicillanic acid with general structure IV may be prepared by treatment of 6-APA with compounds $R^3-Y^1$, where $R^3$ has the same meaning as above, and $Y^1$ is halogen or a functionally equivalent group capable of reacting with a carboxy group under formation of an ester linkage, such as an organic sulphonic acid residue. The reaction is preferably performed in organic solvents, such as dimethylformamide, dimethylsulphoxide, or hexamethylphosphoramide.

Alternatively, 6-acylaminopenicillanic acids with acyl groups that can be removed without destruction of the penicillin ring system are treated with $R^3-Y^1$, wherein $R^3$ and $Y^1$ have the meaning specified above, to give esters of the 6-acylaminopenicillanic acids from which the acyl groups then are removed to give the esters of 6-aminopenicillanic acid of formula III. A preferred method consists of reacting a salt, e.g., the sodium, potassium, or tetraalkylammonium salt, of benzylpenicillin with $R^3-Y^1$ in an organic solvent, such as chloroform, methylenechloride, acetone, dimethylformamide, dimethylsulphoxide, or hexamethylphosphoramide, or in a mixture of an organic solvent and water, e.g., aqueous acetone or dioxane, to give the corresponding ester of benzylpenicillin. The phenylacetyl side chain is then removed, according to the method described in Netherlands patent publication No. 6,401,421 of South African patent publication No. 67/2927, by treatment with phosphorous pentachloride in the presence of a tertiary organic base to give an imino chloride, which is reacted with an alcohol-like propanol to give the corresponding imino ether, which is hydrolyzed by addition of water or alcoholized by addition of alcohol, to give the ester III. Alternatively, the phenylacetyl side chain may be removed by enzymatic hydrolysis using an *E. coli* acylase, according to the method described in French Pat. No. 1,576,027.

In still another method, N-protected 6-aminopenicillanic acids are reacted with $R^3-Y^1$ to give the corresponding ester from which the protecting groups are removed to give the compounds of general formula IV. Examples of protecting groups which can be used are the benzyloxycarbonyl group, which is removed by catalytic hydrogenation, the o-nitrophenylsulphenyl group, which can be removed by treatment with nucleophilic agents at acid pH (Japanese Pat. No. 505,176), and the trityl group, which can be removed by mild acid hydrolysis.

Alternative methods can be used for the preparation of the compounds of the invention. Six-formamidopenicillanic acid may be converted into esters of formula VI

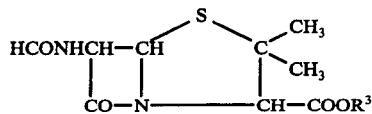

where $R^3$ is as defined above by reaction with $R^3Y^1$ under the conditions previously indicated. Treatment of VI with a 1,1-dihalogendimethyl ether, e.g., 1,1-dichlorodimethyl ester, in the presence of a tertiary organic base, gives a reactive derivative which reacts with an amine of formula VII

where $R^1$ and $R^2$ are as defined above to give the compound of formula I.

A third method consists of reacting compounds of formula II, suitable in form of a salt, e.g., a sodium, potassium, calcium, triethylammonium, or tetraalkylammonium salt, with a compound $R^3Y^1$, wherein $R^3$ and $Y^1$ have the meaning specified above, to give the compounds of the invention with general formula I. The reaction is suitably performed in organic solvents, such as chloroform, methylenechloride, acetone, dimethylformamide, dimethylsulphoxide, or hexamethylphosphoramide, or in aqueous organic solvents, such as aqueous dioxane.

As described above, the starting material may be in the form of a salt, for instance, a sodium, potassium, calcium, or trialkylammonium salt, in some of the ways for the preparation of the compounds of the invention.

In addition, tetralkylammonium salts and other analogues salts, such as salts where the cation has the formula $A^1A^2A^3A^4N \oplus$, in which formula $A^1$ is selected from the group consisting of straight and branched alkyl groups containing from 3 to 6 carbon atoms, substituted and unsubstituted aryl, and substituted and unsubstituted aralkyl, and wherein $A^2$, $A^3$, and $A^4$, which are the same or different, are selected from the group consisting of straight and branched alkyl groups containing from 1 to 6 carbon atoms, provided that $A^2$, $A^3$, and $A^4$ are alkyl with 3 to 6 carbon atoms when $A^1$ is alkyl, may be used.

Illustrative examples of suitable combinations of $A^1$, $A^2$, $A^3$, and $A^4$ in the quaternary ammonium ion $A^1A^2A^3A^4N \oplus$ are given below:

TABLE I

| Examples of suitable combinations of the radicals $A^1$–$A^4$ in the $A^1A^2A^3A^4N \oplus$ ion | | | |
|---|---|---|---|
| $A^1$ | $A^2$ | $A^3$ | $A^4$ |
| n-propyl | n-propyl | n-propyl | n-propyl |
| i-propyl | i-propyl | i-propyl | i-propyl |
| n-butyl | n-butyl | n-butyl | n-butyl |
| i-butyl | i-butyl | i-butyl | i-butyl |
| n-pentyl | n-pentyl | n-pentyl | n-pentyl |
| n-hexyl | n-hexyl | n-hexyl | n-hexyl |
| phenyl | methyl | methyl | methyl |
| phenyl | ethyl | ethyl | ethyl |
| p-tolyl | ethyl | ethyl | ethyl |
| p-chlorophenyl | ethyl | ethyl | ethyl |

When the radicals $A^1$–$A^4$ all are different, the resulting ion contains an asymmetric center and may occur in two enantiomeric forms. Epimeric forms can occur if $A^1$, $A^2$, $A^3$, and/or $A^4$ contain one or more asymmetric carbon atoms.

Examples of quaternary ammonium ions containing an asymmetric center are given in Table II:

TABLE II

| Examples of quaternary ammonium ion $A^1A^2A^3A^4N\oplus$ containing an asymmetric center | | | |
|---|---|---|---|
| $A^1$ | $A^2$ | $A^3$ | $A^4$ |
| benzyl | n-propyl | i-propyl | n-butyl |
| benzyl | n-propyl | i-propyl | sec. butyl |
| benzyl | n-propyl | n-butyl | sec. butyl |
| n-propyl | n-propyl | n-butyl | sec. butyl |
| n-propyl | n-propyl | n-propyl | sec. butyl |
| n-propyl | n-propyl | n-propyl | sec. pentyl |
| n-propyl | n-propyl | n-propyl | sec. hexyl |
| n-propyl | n-propyl | n-butyl | sec. hexyl |

The use, as described above, of a quaternary salt form of the starting material for the preparation of the compounds of this invention is not previously described in the literature pertaining to this technical field. In this method, the preferred cation is the tetraalkylammonium ion, particularly the tetrabutylammonium ion. The preferred solvents are chloroform, methylenechloride, and acetone.

The quaternary ammonium salt form of the above-described starting material may be prepared by reacting the starting material in question with a quaternary ammonium salt of the formula $A^1A^2A^3A^4N \oplus B \ominus$, wherein $A^1$, $A^2$, $A^3$, and $A^4$ have the meanings specified above, and B is a suitable anion, such as $HSO_4 \ominus$, $Cl \ominus$, or $CH_3COO \ominus$, to the formation of a quaternary salt of the starting material.

The salts of the formula above which contain B as the anion may be prepared in known manner analogous, as described in, for instance, Belgian Pat. No. 751,791. The anion $B \ominus$ is in the preferred embodiment $HSO_4 \ominus$.

The following examples will further illustrate the invention.

EXAMPLE 1

1'-Ethoxycarbonyloxy-ethyl 6-(hexahydro-1H-azepin-1-yl)-methyleneaminopenicillanate One-hexamethyleneiminocarboxaldehyde-dimethylacetate (3.1 g) in chloroform (50 ml) was added dropwise at $-30°$ C. to a solution of 1'-ethoxycarbonyloxy-ethyl 6-aminopenicillanate (5 g) and triethylamine (1.9 ml) in chloroform (150 ml) during 15 minutes. Then, the temperature is allowed to rise to 0° during 30 minutes, and the mixture is stirred at 0° for another 60 minutes. Water (120 ml) is added, and stirring is continued for 10 minutes. The water phase is separated and the organic layer is washed with water and stripped. The residue (5 g) showed a strong IR-absorption band at 1775 cm$^{-1}$ ($\beta$-lactam ring).

Incubation of the product with human serum at 37° C. was found to cause a rapid formation of 6-(hexahydro-1H-azepin-1-yl)-methyleneaminopenicillanic acid.

The 1'-ethoxycarbonyloxy-ethyl 6-aminopenicillanate was prepared, as described in Swedish patent application No. 12688/70.

EXAMPLE 2

By substituting the 1'-ethoxycarbonyloxy-ethyl 6-aminopenicillanate in example 1 with 1'-acetoxy-ethyl 6-aminopenicillanate and ethoxycarbonyloxymethyl 6-aminopenicillanate, 1'-acetoxy-ethyl and ethoxycarbonyloxymethyl six-(hexahydro-1H-azepin-1-yl)-methyleneaminopenicillanate, respectively, were obtained. The compounds showed strong β-lactam absorption in IR at 1775 cm$^{-1}$ and were rapidly hydrolyzed by human serum to the corresponding penicillanic acids.

EXAMPLE 3

1'-Ethoxycarbonyloxyethyl 6-(piperidyl-1-)-methyleneaminopenicillanate

One'-ethoxycarbonyloxyethyl benzylpenicillanate (3.2 g, 0.007 mole) was added, with stirring and chilling to −40° C., to phosphorous pentachloride (1.7 g, 0.008 mole) and quinoline (1.8 g, 0.016 mole) in dry methylene chloride (50 ml). The reaction was kept in dry inert gas (argon). After one hour, dry methanol (2.24 g) was added dropwise, and the temperature was adjusted to −30° C. After one hour, brine (15 ml) was dropped to the solution, while the temperature was allowed to rise to 0°. After 15 minutes, the organic phase was dried and evaporated in vacuo, the residue was triturated with petroleum ether and dried, yielding a crystalline mass (2.8 g, 100%), IR 1790 cm$^{-1}$ (β-lactam). To a solution of this material (2.8 g, 0.007 mole) and triethylamine (0.84 ml, 0.006 mole) in chloroform (50 ml) at −50° C. to −60° C., N-piperidylchloroformiminiumchloride (1.1 g, 0.006 mole) in chloroform (20 ml) was added dropwise. The mixture was kept under dry argon for 1.5 hours, during which time the temperature rose to 0°. The solvent was removed in vacuo at 40° and the residue was slurried with dry acetone (100 ml) and filtered. The filtrate was concentrated in vacuo and the remaining oil was triturated with petroleum ether until crystallization, yield 1.2 g, IR-absorption 1760 cm$^{-1}$ (β-lactam, NMR: ringlet at 480 cps (methylenemino), multiplet at 320 cps (5- and 6-position of penicillin nucleus).

EXAMPLE 4

One'-acetoxyethyl 6-(piperidyl-1)-methyleneaminopenicillanate was prepared, as described in example 3, from 1'-acetoxyethyl benzylpenicillanate (2.94 g, 0.007 mole) and N-piperidylchloroformiminiumchloride (1.1 g, 0.006 mole), yielding a half crystalline mass. IR-absorption at 1760 cm$^{-1}$ (β-lactam).

EXAMPLE 5

Ethoxycarbonyloxymethyl 6-(hexahydro-1H-azepin-1-yl)-methyleneaminopenicillanate was prepared, as described in example 3, from ethoxycarbonyloxymethyl benzylpenicillanate (3. g, 0.007 mole) and hexahydro-1H-azepin-1-yl-chloroformiminiumchloride (1.15 g, 0.006 mole), yielding an oil. IR-absorption 1760 cm$^{-1}$ (β-lactam).

EXAMPLE 6

Phenoxycarbonyloxymethyl 6-(ethyl-isopropyl)-methyleneaminopenicillanate was prepared, as described in example 3, from phenoxycarbonyloxymethyl benzylpenicillanate (3.4 g, 0.007 mole) and N-ethyl-N-isopropylchloroformiminiumchloride (1.02 g, 0.006 mole), yielding an oil product. IR-absorption 1775 cm$^{-1}$ (β-lactam).

EXAMPLE 7

Phenoxycarbonyloxymethyl 6-(N,N-dimethyl)-methyleneaminopenicillanate was prepared, as described in example 3, from phenoxycarbonyloxymethyl benzylpenicillanate (3.4 g, 0.007 mole) and N,N-dimethylchloroformiminiumchloride (0.77 g, 0.006 mole), yielding a half crystalline mass. IR-absorption 1775 cm$^{-1}$ (β-lactam).

EXAMPLE 8

2'-Ethyl-hexyloxycarbonyloxy-methyl 6-(Hexahydro-1H-azepin-1-yl-methyleneamino)-penicillanate To an ice cold solution of potassium benzylpenicillinate (18.6 g, 0.05 mol) in 50 ml of DMF was added chloromethyl 2-ethyl-hexyl carbonate (11.0 g, 0.05 mol) dissolved in 50 ml of DMF during 15 minutes. The solution was stirred over night. The reaction mixture was poured into 200 ml of saturated sodium bicarbonate solution and extracted with 3×200 ml of ethylacetate. The combined organic extracts were washed with 3×200 ml of dilute sodium bicarbonate, 50 ml of saturated brine, dried over MgSO$_4$ and evaporated in vacuo to give 17.0 g of an oil. The residue was washed repeatedly by decantation with petroleum ether and dissolved in ethyl acetate, stirred with 1 g of activated carbon, filtered and evaporated in vacuo to give 5.3 g of an oily residue. Thin layer chromatography (Ethyl acetate-Silica Gel) showed three sports in UV. 2'-Ethyl-hexyloxycarbonyloxymethyl benzylpenicillinate (4.7 g) (R$_f$ 0.67) was isolated by column chromatography. The product showed strong IR-absorption at 1790–1740 and 1670 cm$^{-1}$ due to β-lactam, ester carbonyls and amide respectively.

NMR (CDCl$_3$) = 0.70–2.10 (m), 15 H; 1.40 (s) 6H; 3.58 (s) 2H; 4.00–4.40 (m) 2 H; 4.32 (s) 1 H; 5.41 (d) J = 4 Hz 1 H; 5.62 (q) J$_1$ = 4Hz, J$_2$ = 7 Hz 1 H; 5.65 (s) 2 H; 6.35 (d) J = 7 Hz 1 H; 7.20 (s) 5 H.

To a stirred solution of PCl$_5$ (2.1 g, 10 mmol) in dry ethanol-free chloroform (25 ml) quinoline (2.0 g, 20 mmol) was added and after cooling to −15°, 2'-ethyl-hexyloxycarbonyloxy-methyl-benzylpenicillinate (4.5 g, 8.8 mmol) dissolved in chloroform (10 ml). After stirring for 15 min at −15°, n-propanol (7.5 ml, 100 mmol) was added over a period of 10 minutes. The mixture was kept at −10° for a further 15 min, then saturated brine (25 ml) was added with vigorous stirring. After 15 min at −10°, petroleum ether (2000 ml) was added and the mixture was kept at −10° for 1 hour. 2'-Ethyl-hexyloxycarbonyloxy-methyl 6-aminopenicillanate hydrochloride was obtained as a yellow semisolid precipitate directly used for the following step.

A dry solution of 2'-ethyl-hexyloxycarbonyloxy-methyl 6-aminopenicillanate hydrochloride in ethanol-free chloroform was cooled to −30° C with stirring under dry inert argon. 2.83 ml (0.0203 mol) of triethylamine was added. A solution of 1.76 g (0.00967 mol) hexahydroazepinforminimium chloride in 7.5 ml of dry ethanol-free chloroform was added with stirring during 20 min and the temperature kept at −25° C. The mixture was stirred with ice-cooling for an additional 30 minutes. The solution was evaporated in vacuo at +20°. Triethylamine hydrochloride was precipitated by triturating the residue with 30 ml of acetone. The precipitate was filtered off and the solution evaporated in vacuo at +20°. The residue was triturated with 2×50 ml of petroleum ether, evaporated and dissolved in 10 ml of 4 methyl-2-pentanone. After keeping the solution at +3° C over night 2'-ethyl-hexyloxycarbonyloxy-methyl 6-(hexahydro-1H-azepin-1-yl)-methyleneamino-penicillanate was obtained as a precipitate. Mp 119°–121° C. IR:

strong absorption at 1760 cm$^{-1}$, 1785 cm$^{-1}$ and 1690 cm$^{-1}$ due to β-lactam, carbonate and ester carbonyls and to the imino group.

EXAMPLE 9

Pharmaceutical formulations

For preparation of tablets, the following compositions were made:

| | | |
|---|---|---|
| a) | 1'-acetoxyethyl 6-hexahydro-1H-azepin-1-(yl)-methyleneaminopenicillanate | 325 mg |
| | Starch | 100 mg |
| | Magnesium stearate | 10 mg |
| b) | 1'-ethoxycarbonyloxyethyl 6-hexahydro-1H-azepin-1-(yl)-methylenaminopenicillanate | 350 mg |
| | Starch | 100 mg |
| | Magnesium stearate | 10 mg |
| c) | Ethoxycarbonyloxymethyl 6-hexahydro-1H-azepin-1-(yl)-Methyleneaminopenicillanate | 350 mg |
| | Calcium carbonate | 100 mg |
| | Magnesium stearate | 10 mg |
| d) | 1'-ethoxycarbonyloxyethyl 6-(piperidyl-1)-methyleneaminopenicillanate | 350 mg |
| | Lactose | 100 mg |
| | Magnesium stearate | 10 mg |
| e) | 1'-acetoxyethyl 6-(piperidyl-1)-methyleneaminopenicillanate | 300 mg |
| | Calcium carbonate | 100 mg |
| | Lactose | 100 mg |
| | Magnesium stearate | 10 mg |

For filling in capsules, the following formulations were made:

| | | |
|---|---|---|
| f) | 1'-acetoxyethyl 6-hexahydro-1H-azepin-1-(yl)-methyleneaminopenicillanate | 350 mg |
| | Magnesium stearate | 5 mg |
| g) | 1'-ethoxycarnbonyloxyethyl 6-hexahydro-1H-azepin-1-(yl)-methyleneamino-penicillanate | 350 mg |
| | Lactose | 40 mg |
| | Magnesium stearate | 5 mg |

For oral suspensions, the following formulations were made:

| | | |
|---|---|---|
| h) | 1'-acetoxyethyl 6-(piperidyl-1)-methyleneaminopenicillanate | 35 mg |
| | Aluminum monostearate | 50 mg |
| | Tween-80 ® | 1.2 mg |
| | Peanut oil | ad 1000 mg |
| i) | 1'-ethoxycarbonyloxyethyl 6-hexahyddro- | 36 g |

| | |
|---|---|
| 1H-azepin-1-(yl)-methyleneamino-penicillanate | |
| Sodium benzoate | 0.48 g |
| Sodium chloride | 0.75 g |
| Flavoring agents | 4.7 g |
| Aerosil ® | 0.3 g |
| Antifoam ® | 0.0375 g |
| Alkali salts of polysaccharide sulphates | 4.0 g |
| Sodium saccharinate | 0.4 g |
| Sorbitol | ad 100 g |

We claim:

1. A compound of the structural formula

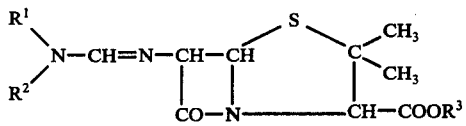

or a therapeutically acceptable salt thereof, wherein $R^1$ and $R^2$, together with the adjacent nitrogen atom, form a heterocyclic ring structure having the formula

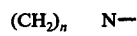

wherein $n$ is 3–6, $R^3$ is the radical

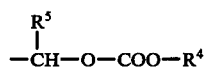

in which radical $R^4$ is selected from the group consisting of alkyl groups containing from 1 to 8 carbon atoms, and $R^5$ is hydrogen or methyl.

2. A compound, according to claim 1, which contains one or more asymmetrical centers in the form of a pure stereoisomer.

3. A compound, according to claim 1, having the formula

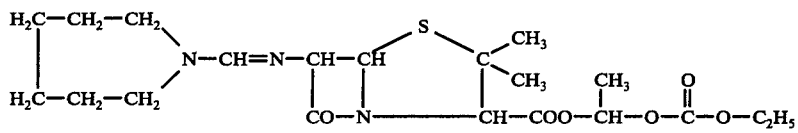

or a therapeutically acceptable salt thereof.

4. A compound, according to claim 1, having the formula

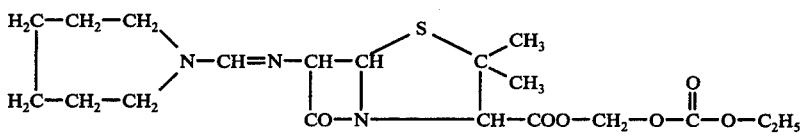

or a therapeutically acceptable salt thereof.

5. A compound, according to claim 1, having the formula

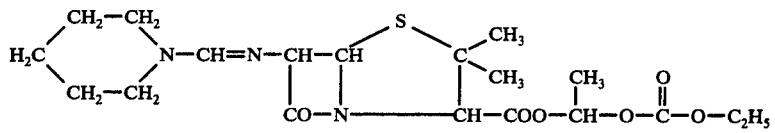

or a therapeutically acceptable salt thereof.

6. A pharmaceutical preparation for the treatment of bacterial infection which comprises, as an active ingredient, a therapeutically effective amount of at least one compound of the structural formula

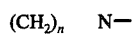

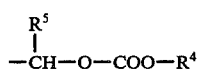

or a therapeutically acceptable salt thereof, wherein $R^1$ and $R^2$, together with the adjacent nitrogen atom, form a heterocyclic ring structure having the formula $(CH_2)_n$   N— wherein n is 3–6, $R^3$ is the radical $$-\overset{R^5}{\underset{|}{CH}}-O-COO-R^4$$

in which radical $R^4$ is selected from the group consisting of alkyl groups containing from 1 to 8 carbon atoms, and $R^5$ is hydrogen or methyl, in association with a pharmaceutically acceptable carrier.

7. A pharmaceutical preparation, according to claim 6, containing, as active ingredient, a compound which contains one or more asymmetric centers in the form of a pure stereoisomer.

8. A pharmaceutical preparation, according to claim 6, containing, as active ingredient, a compound having the formula

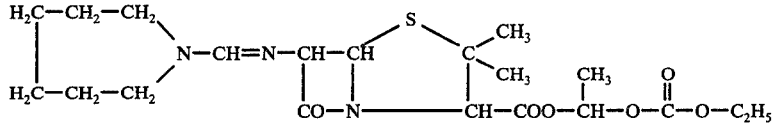

or a therapeutically acceptable salt thereof.

9. A pharmaceutical composition, according to claim 6, containing, as active ingredient, a compound having the formula

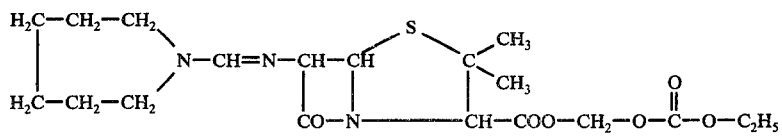

or a therapeutically acceptable salt thereof.

10. A pharmaceutical preparation, according to claim 6, containing, as active ingredient, a compound having the formula

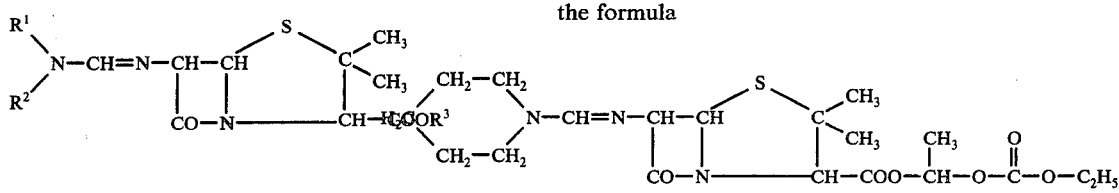

or a therapeutically acceptable salt thereof.

11. A method for the treatment of bacterial infection in man or animals which comprises administering to a host suffering from such infection an anti-bacterially effective amount of a compound of the structural formula

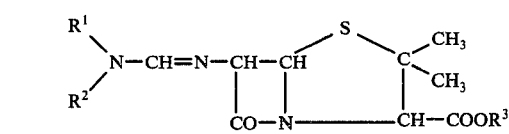

or a therapeutically acceptable salt thereof, wherein $R^1$ and $R^2$, together with the adjacent nitrogen atom, from a heterocyclic ring structure having the formula $(CH_2)_n$   N— wherein n is 3–6, $R^3$ is the radical $$-\overset{R^5}{\underset{|}{CH}}-O-COO\ R^4$$

in which radical $R^4$ is selected from the group consisting of alkyl groups containing from 1 to 8 carbon atoms, and $R^5$ is hydrogen or methyl.

12. A method, according to claim 11, wherein said therapeutically effective compound is

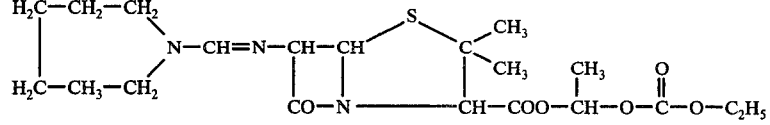

or a therapeutically acceptable salt thereof.

13. A method, according to claim 11, wherein said therapeutically effective compound is

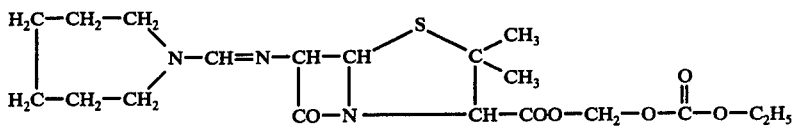

or a therapeutically acceptable salt thereof.

14. A compound of the structural formula

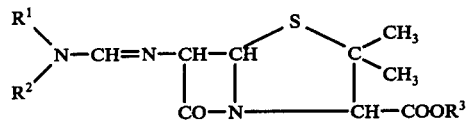

or a therapeutically acceptable salt thereof, wherein $R^1$ and $R^2$, together with the adjacent nitrogen atom, form a heterocyclic ring structure having the formula

and $R^3$ is the radical

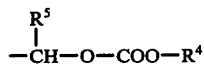

in which radical $R^4$ is selected from the group consisting of alkyl groups containing from 1 to 8 carbon atoms, and $R^5$ is hydrogen or methyl.

15. A compound according to claim 14, 1'-ethoxycarbonyloxyethyl 6β-[(hexahydro-1 (2H)-azocinyl)-methyleneamino]penicillanate or a therapeutically acceptable salt thereof.

16. A compound according to claim 14, ethoxycarbonyloxymethyl 6β-[(hexahydro-1 (2H)-azocinyl)-methyleneamino]penicillanate or a therapeutically acceptable salt thereof.

17. A pharmaceutical preparation for the treatment of bacterial infection which comprises, as an active ingredient, a therapeutically effective amount of at least one compound of the structural formula

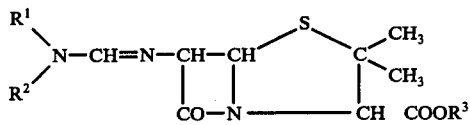

or a therapeutically acceptable salt thereof, wherein $R^1$ and $R^2$, together with the adjacent nitrogen atom, form a heterocyclic ring structure having the formula

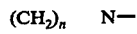

and $R^3$ is the radical

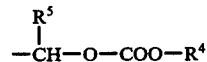

in which radical $R^4$ is selected from the group consisting of alkyl groups containing from 1 to 8 carbon atoms, and $R^5$ is hydrogen or methyl in association with a pharmaceutically acceptable carrier.

18. A pharmaceutical preparation according to claim 17 wherein the active ingredient is 1'-ethoxycarbonyloxyethyl 6β-[(hexahydro-1(2H)-azocinyl)-methyleneamino]-penicillanate or a therapeutically acceptable salt thereof.

19. A pharmaceutical preparation according to claim 17 wherein the active ingredient is ethoxycarbonyloxymethyl 6β-[(hexahydro-1(2H)-azocinyl)-methyleneamino]-penicillanate or a therapeutically acceptable salt thereof.

20. A method for the treatment of bacterial infection in man and animals which comprises administering to a host suffering from such infection an anti-bacterially effective amount of a compound of the structural formula

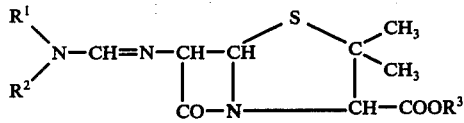

or a therapeutically acceptable salt thereof, wherein $R^1$ and $R^2$, together with the adjacent nitrogen atom, form a heterocyclic ring structure having the formula

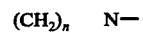

and $R^3$ is the radical

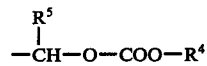

in which radical $R^4$ is selected from the group consisting of alkyl groups containing from 1 to 8 carbon atoms, and $R^5$ is hydrogen or methyl.

21. A method according to claim 20 wherein the compound is 1'-ethoxycarbonyloxyethyl 6β-[(hexahydro-1(2H)-azocinyl)-methyleneamino]-penicillanate or a therapeutically acceptable salt thereof.

22. A method according to claim 20 wherein the compound is ethoxycarbonyloxymethyl 6β-[(hexahydro-1(2H)-azocinyl)-methyleneamino]-penicillanate or a therapeutically acceptable salt thereof.

* * * * *

UNITED STATES PATENT OFFICE
CERTIFICATE OF CORRECTION

Patent No. 4,089,963        Dated May 16, 1978

Inventor(s) Peter Bamberg et al.

It is certified that error appears in the above-identified patent and that said Letters Patent are hereby corrected as shown below:

First Page, after "Item [58]" insert --Foreign Application Priority Data March 13, 1972 United Kingdom.......11689/72--;
Column 6, line 45, "of" should be --or--;
Column 10, line 26, "sports" should be --spots--;

Column 11, line 34, "ethoxycarnbonyloxyethyl" should be --ethoxycarbonyloxyethyl--;
Column 11, line 61, "6-hexahyddro-" should be --6-hexahydro- --;
Column 12, line 25, "$(CH_2)_n$    N- " should be $$--(CH_2)_n\phantom{x}N---;$$

Column 13, claim 6, formula is unreadable by overlapping of formula of claim 10;
Column 13, line 33, "$(CH_2)_n$    N- " should be $$--(CH_2)_n\phantom{x}N---;$$

Column 14, claim 10, the beginning of the formula is unreadable by overlapping of the formula of claim 6;
Column 14, line 40, "$(CH_2)_n$    N- " should be $$--(CH_2)_n\phantom{x}N---;$$

UNITED STATES PATENT OFFICE
CERTIFICATE OF CORRECTION

Patent No. 4,089,963   Dated May 16, 1978

Inventor(s) Peter Bamberg et al.

It is certified that error appears in the above-identified patent and that said Letters Patent are hereby corrected as shown below:

Column 14, claim 12, line 3, the portion of the formula reading

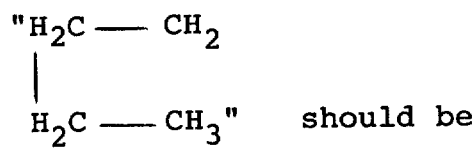

should be

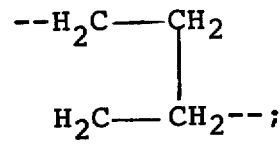

Column 15, line 25, "$(CH_2)_n \quad N-$" should be

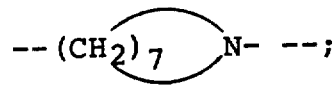

Column 15, line 60, "$(CH_2)_n \quad N-$" should be

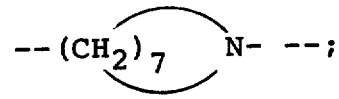

UNITED STATES PATENT OFFICE
CERTIFICATE OF CORRECTION

Patent No. 4,089,963  Dated May 16, 1978

Inventor(s) Peter Bamberg et al.

It is certified that error appears in the above-identified patent and that said Letters Patent are hereby corrected as shown below:

Column 16, line 45, "$(CH_2)_n$ N-" should be -- $(CH_2)_7$ N- --.

Signed and Sealed this

Seventeenth Day of April 1979

[SEAL]

Attest:

RUTH C. MASON  
Attesting Officer

DONALD W. BANNER  
Commissioner of Patents and Trademarks